United States Patent [19]
Payne et al.

[11] Patent Number: 5,821,206
[45] Date of Patent: Oct. 13, 1998

[54] COMPOSITION

[75] Inventors: Richard Payne, Manasquan; AnBen Hwang, Verona; Ravi Subramanvam, Belle Mead, all of N.J.

[73] Assignee: Colgate Palmolive Company, New York, N.Y.

[21] Appl. No.: 790,636

[22] Filed: Jan. 29, 1997

Related U.S. Application Data

[60] Provisional application No. 60/010,841, Jan. 30, 1996.

[51] Int. Cl.$^6$ .................................................. C11D 17/00
[52] U.S. Cl. ......................... 510/141; 510/447; 510/505
[58] Field of Search ........................... 510/152, 447–481, 510/505, 141

[56] References Cited

U.S. PATENT DOCUMENTS

| | | | |
|---|---|---|---|
| 3,644,482 | 2/1972 | Dexter et al. | 260/473 |
| 4,077,911 | 3/1978 | Okumura et al. | 252/550 |
| 4,282,163 | 8/1981 | Suzuki et al. | 260/409 |
| 5,204,022 | 4/1993 | Sharma | 252/363.5 |
| 5,478,485 | 12/1995 | Bialas et al. | 252/86 |
| 5,496,555 | 3/1996 | Colwell | 424/405 |
| 5,594,055 | 1/1997 | Young | 524/291 |
| 5,614,648 | 3/1997 | Greene et al. | 554/4 |

FOREIGN PATENT DOCUMENTS

| | | | |
|---|---|---|---|
| 195 16 698 A1 | 11/1996 | Germany . | |
| 49/96072 | 9/1974 | Japan . | |
| 58/177475 | 10/1983 | Japan . | |
| 61/238900 | 10/1986 | Japan . | |
| 91/16372 | 10/1991 | WIPO . | |
| 93/07209 | 4/1993 | WIPO . | |
| WO 93/23515 | 11/1993 | WIPO . | |

OTHER PUBLICATIONS

Irganox 1076 Antioxidant and Thermal Stabilizer, Ciba–Geig4, p. 1–11.

Mitsui Toastu, "Stabilized Method Mono Ethanolamine Comprise Add Antioxidant Mono Ethalamine Solvent Contain Mono Ethalamine High Deteriorate Resistance Clean Agent," *Derwent Abstract*, Dec. 19, 1995.

*Primary Examiner*—Douglas J. McGinty
*Assistant Examiner*—John R. Hardee
*Attorney, Agent, or Firm*—Martin B. Barancik

[57] ABSTRACT

A cleansing composition which comprises a cleansing effective amount of one of a mixture of a surfactant chain and a color stabilizing effective amount of a compound of the formula

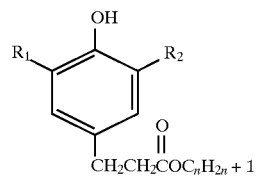

wherein R1 and R2 are the same or different and are isopropyl or tertiary butyl and n is an integer of about 8 to about 20.

22 Claims, No Drawings

COMPOSITION

This application claims the benefit of U.S. Provisional application No. Ser. No. 60/010,841 filing date Jan. 30, 1996.

BACKGROUND OF THE INVENTION

Soap has been used for time memorial to cleanse human skin. Both solid and liquid compositions containing soap have been used to deliver the surfactant to the skin for cleansing purposes. As with virtually every composition used for consumer purposes, the stability of the composition is critical for proper use and/or prolonged storage prior to use.

It is well known that free radical reactions will interfere with the stability of soap containing compositions. Free radicals initiate chain reactions which bring about the deterioration of long chain hydrocarbon materials such as soaps, free fatty acids, synthetic surfactants and the like present in cleansing compositions. Such reactions can bring about among other observable effects, color changes in the cleansing composition and eventually the rancidification of the formulation caused by the presence of breakdown products which are highly odiferous.

The deterioration of the long chain hydrocarbon containing materials can be substantially hindered by the use of known materials to either hinder the catalyzation of certain free radical mechanisms or work as a free radical sink to terminate the free radical chain reaction by rendering the chain free radical harmless. Example of the former type of materials are agents which chelate metals such as copper and iron which are known catalyzers of free radical initiation steps, particularly at points of unsaturation in the hydrocarbon chain. Such agents include ethylene diamine tetra carboxylic acid and its salts and various salts of phosphonic acid derivatives. Exemplary of the free radical sinks are various aromatic compounds which seems to work as a sink for the generated free radials whatever their initial mode of propagation might be. A prime example of this type of compound which has been in use for several decades is butylated hydroxy toluene, (usually known by its abbreviation BHT).

However, even with the use of BHT, stability problems are known to occur. General discoloration of cleansing bars occurs from time-to-time as well as specific points of coloring, usually intensely yellow also occurs. Although unusual, after prolonged periods of time, odors from a soap bar can also occur. Therefore, a need for a better cleansing formulation, particularly solid, stability enhancing additive remains.

SUMMARY OF THE INVENTION

In accordance with the invention, there is a personal care cleansing composition which comprises a cleansing effective amount of a long chain alkyl or alkenyl containing surfactant or mixtures thereof and a color stabilizing effective amount of a compound of the formula

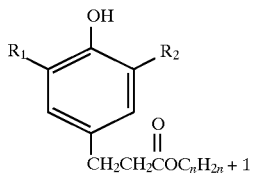

wherein R1 and R2 are the same or different and are isopropyl or tertiary butyl and n is about 8 to about 20.

A preferred composition is one wherein the surfactant is a soap.

A further preferred composition is a solid, more preferably a bar.

DETAILED DESCRIPTION OF THE INVENTION

Any surfactant may be used in the cleansing composition which removes soil from skin and which is susceptible to degradation upon prolonged shelf-life, particularly with respect to degradation which leads to discoloration and/or unpleasant odors. Therefore, any surfactant which has a long chain alkyl or alkenyl group or mixtures thereof, can be susceptible to such degradation. By long chain is meant at least about 8 carbon atoms, preferably 10, usually, normal or having a slight amount of branching. Generally, the maximum number of carbon atoms is not significant but usually above 20 is not preferred. Small quantities of olefinic bond(s) can be present in the predominantly alkyl sections, particularly if the source of the "alkyl" group is obtained from a natural product such as tallow, coconut oil and the like.

Soap, a long chain alkyl or alkenyl, branched or normal carboxylic acid salt such as sodium, potassium, ammonium or substituted ammonium salt can be present in the composition and is preferred.

Examples of such surfactants are the anionic, amphoteric, nonionic and cationic surfactants. Examples of anionic zwitterionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

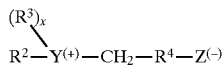

$$R^2-Y^{(+)}-CH_2-R^4-Z^{(-)}$$
with $(R^3)_x$ on $Y$ wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di- methyl-N-hexadecylammonio)propane-1-sulfonate; 3-(N,N-dimethyl-N-hexadecylammonio )-2-hydroxypropane-1-sulfonate; 4-( N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N,-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxylate, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072 N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl)amine oxide, dimethyloctylamine oxide, dimethyldecylamine oxide, dimethyltetradecylamine oxide, 3,6,9 trioxaheptadecyldiethylamine oxide, di(2-hydroxyethyl)tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

RR'R"P→O wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Any quantity of surfactant or mixture of surfactant which brings about a skin cleansing effect can be employed in the composition of this invention. Generally, at least about 1 wt. % of the composition should be surfactant. Preferred minimums of at least about 3, 5, 7, 10, 20 and 30 wt. % surfactant(s) can be present in the composition. Maximum quantities of surfactant(s) depends upon the physical nature of the composition being employed. Generally, no more than about 95–97 wt. % surfactant(s) are present, specifically no more than about 90 wt. % surfactant(s). Maximum quantities of about 20, 30, 40, 50, 60, 70, 80, or 85 wt. % surfactant(s) can also be readily employed.

The anionic surfactant can be present in the composition in various preferred quantities beyond those general quantities previously discussed for all surfactants of from about 1 to about 96 wt. %, specifically about 5 to about 85 wt. %. With respect to liquid, preferably aqueous, compositions, the anionic surfactant(s) is from about 2 to about 20 wt. % of the composition, specifically about 5 to about 15 wt. %. For a solid composition, the anionic surfactant(s) can be from about 5 to about 90 wt. %, preferably from about 10 to about 50 wt. % for a "syndet" bar, about 55 to about 80 wt. % for a "combar", and about 70 to about 90 wt. %, more preferably about 75 to about 85 wt. % in a solid composition wherein there is only one anionic surfactant therein, such as soap.

The antioxidant of the formula is specifically one where all the "R" groups are the same and most preferably are all tertiary butyl. When the "R" groups are each tertiary butyl and n is 18, the compound is available from Ciba-Geigy as Irganox 1076. The CAS number is 2082-79-3 and its chemical name is octadecyl (3,5-di-tert-butyl-4-hydroxyhydrocinnamate). The quantity of antioxidant percent in the compositions(s) of the invention is an amount effective to provide color stability to the composition showing shelf aging. The upper limit appears to be primarily dependent upon the cost of the material. In solid compositions, generally from about 25 to about 500 ppm of the composition can be employed, preferably from about 50 to about 300 ppm of the composition. In liquid compositions and generally from about 10 to about 300 ppm of the antioxidant can be employed, preferably from about 25 to about 250 ppm of the composition.

The physical nature of the composition is not critical and can be a solid, liquid or gel. The method of making such a composition is by the usual methods employed in the detergent industry. The antioxidant is added at the usual point an antioxidant is added in the process.

Below are standard liquid and solid compositions as illustrative examples of the composition(s).

| Solid Soap Bar Formula | |
|---|---|
| Component | % By Weight |
| Mixture of Sodium Tallowate, Cocoate, Palmate, and Palm Kernelate soaps | 80–87 |
| Water | 8–10 |
| Glycerine | 0.5–1.5 |
| Frangrance/Dyes | Q.S. |
| Versenex 80-DTPA (40%) | 0.2 |
| Titanium Dioxide | 0.2 |
| Citric Acid (50%) | 0.25 |
| Sodium Chloride | 0.05–1.3 |
| Antioxidant (Irganox 1076) | 0.0025–0.1 |

| Liquid | |
|---|---|
| Component | % By Weight |
| Alpha Olefin Sulfonate (40%) | 10.0 |
| Ammonium Lauryl Sulfate (28%) | 25.0 |
| Cocamidopropyl Hydroxy Sultaine (50%) | 3.5 |
| Versene 100 (Dow) EDTA (39%) | 0.2 |
| Propylene Glycol | 1.0 |
| Lauryl diethanolamide | 0.5 |
| Chloroxylenol | 1.0 |
| Citric Acid | Q.S. to pH 5.5–6.5 |
| Fragrance, Dye(s), Preservative | Q.S. |
| Sodium Chloride | 0.05–0.50 |
| Water | 58.5 |
| Antioxidant (Irganox 1076) | 0.001–0.05 |

The compounds of the invention are not restricted to only personal care cleansing compositions. These compounds can also be useful in oral compositions designed for cleansing teeth.

Organic surface-active agents are used in oral compositions to achieve increased prophylactic action, assist in achieving thorough and complete dispersion of any active material such as an anticalculus agent throughout the oral cavity, as well as rendering the compositions more cosmetically acceptable. The organic surface-active material is preferably anionic, nonionic, or ampholytic in nature, and it is preferred to employ as the surface-active agent a detersive material which imparts to the composition detersive and foaming properties. Suitable examples of anionic surfactants are water-soluble salts or higher fatty acid monoglyceride monosulfates, such as the sodium salt of the monosulated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmittoyl sarcosine which should be substantially free from soap or similar higher fatty acid material. The use of such sarcosinate compounds in certain oral compositions is particularly advantageous since these materials exhibit a prolonged and marked effect in the inhibition of acid formation in the oral cavity due to carbohydrate break down in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoixde (e.g. Pluronic materials).

Generally, surfactants are present in the paste, gel or the typical teeth cleansing composition in from about 1 to about 15 wt % of the composition. The antioxidant of the present invention can also provide stabilization properties to oral compositions containing a peroxide such as hydrogen peroxide or calcium peroxide and the like. The quantity of antioxidant employed is that amount sufficient to stabilize the composition, for example, as a free radical scavenger. Exemplary of such quantities are antioxidant of from about 50 to about 5000 ppm, preferably about 100 to about 2000 ppm of the composition.

The following are examples of the invention which are intended to show the extent of the invention and not be unduly limited thereof.

The following test system was employed to initially look at material which could be useful in surfactant cleansing systems, particularly soap containing systems.

TEST METHOD

An equal amount of potential antioxidant under evaluation and benzoyl peroxide (weight basis) are dissolved into an inert organic solvent such as chloroform to form a 1% (each) solution. 10 ml. of the solution is transferred into a round bottom flask, and heated to boiling under a water cooled condenser. The content is kept refluxing for 15 hours. After removal from heat and allowing to cool to room temperature, the solution is visually inspected for discoloration. This system is designed to bring about yellowing and discoloration which is normally observed in BHT containing cleansing systems.

TEST RESULT

The following materials evaluated show a varied degree of color instability:

Irganox 1076 is more stable than Irganox 1330, which is more stable than Casamine OTB which is more stable than BHT.

a. Irganox 1330 is 1,3,5-trimethyl-2,4,6-tris(3,5-di-tert. butyl-4-hydroxybenzyl) benzene.

b. Casamine OTB is ortho-tolyl biguanide

The BHT is bright yellow after the test period. The Irganox 1330 and Casamine OTB have varying coloration. Irganox 1076 does not show any discoloration after the test period.

When used in a solid, gel, or liquid composition it is preferred to maintain the system essentially absent from free alkali.

The excess alkali in soap formulations can be effectively neutralized by the in-situ "superfatting" with strong acids or with free fatty acids. Any quantity of acid which brings about at least essential neutralization of the free alkali can be employed. Quantities of free acid such as citric, acetic, and tartaric as low as about 0.1 wt. % can be employed with effectiveness. The amount of free fatty acid can also vary considerably although generally at least about 3 or 5 wt. % free fatty acid such as stearic, coco, myristic and the like can be employed, preferably at least about 7 wt. % of the composition. The final pH of the composition, as measured by 1 wt. % solid composition in water is generally from about 6.5 to about 10.3. Too acidic a pH should be avoided as well since compound cleavage can also occur.

We claim:

1. A solid cleansing composition which comprises at least one wt. % of one or a mixture of surfactants about 25 and to about 500 ppm of a compound of the formula

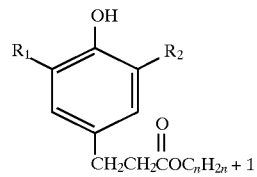

wherein R1 and R2 are the same or different and are isopropyl or tertiary butyl and n is an integer of about 8 to about 20.

2. The composition in accordance with claim 1 wherein each R group is the same.

3. The composition in accordance with claim 2 wherein each R group is tertiary butyl.

4. The composition in accordance with claim 3 wherein the solid can be hand held.

5. The composition in accordance with claim 4 wherein the solid is in a bar shape.

6. The composition in accordance with claim 3 wherein the compound is present in the composition in from about 25 to about 500 ppm of the composition.

7. The composition in accordance with claim 6 wherein the compound is present in the composition in from about 50 to 300 ppm.

8. The composition in accordance with claim 5 wherein the compound is present in from about 50 to about 300 ppm.

9. The composition in accordance with claim 3 wherein essentially all of the free alkali in the composition is neutralized.

10. The composition in accordance with claim 5 wherein essentially all the free alkali in the composition is neutralized.

11. The composition in accordance with claim 3 wherein there is sufficient strong acid, free fatty acid or mixtures thereof to essentially overcome the hydrolytic effects of free alkali on the compound.

12. The composition in accordance with claim 5 wherein there is sufficient strong acid, free fatty acid or mixtures thereof to essentially overcome the hydrolytic effects of free alkali on the compound.

13. The composition in accordance with claim 5 wherein the pH of the bar, as measured in a 1% solution in water is about 6.5 to about 10.3.

14. The composition in accordance with claim 5 wherein the surfactant is soap.

15. The composition in accordance with claim 14 wherein the compound is present in from about 25 to about 500 ppm of the composition.

16. The composition in accordance with claim 15 wherein there is sufficient acid to essentially neutralize any free alkali present.

17. The composition in accordance with claim 16 wherein the pH of the solid, as measured in a 1% solution in water is from about 6.5 to about 10.3.

18. The composition in accordance with claim 3 wherein the cleansing composition is suitable for cleansing teeth.

19. The cleansing composition in accordance with claim 1 suitable for cleansing the oral cavity.

20. The cleansing composition in accordance with claim 19 suitable for cleansing teeth found in the oral cavity.

21. An aqueous liquid cleansing composition which comprises about 2 to about 20 wt % of one or a mixture of non-soap anionic surfactants and about 10 to about 300 ppm of a compound of the formula:

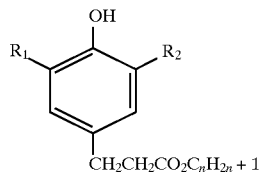

wherein $R_1$ and $R_2$ are the same or different and are isopropyl or tertiary butyl and n is an integer of about 8 to about 20.

22. The composition in accordance with claim 21 wherein the anionic surfactant has an alkyl group of about 8 to about 20 carbon atoms, inclusive.

* * * * *

UNITED STATES PATENT AND TRADEMARK OFFICE
CERTIFICATE OF CORRECTION

PATENT NO. : 5,821,206
DATED : October 13, 1998
INVENTOR(S) : Richard Payne, et. al.

It is certified that error appears in the above-identified patent and that said Letters Patent is hereby corrected as shown below:

Title page, item [75], "Subramanvam" should read -- Subramanyam--.

Signed and Sealed this

Ninth Day of February, 1999

Attest:

Attesting Officer

Acting Commissioner of Patents and Trademarks